United States Patent
Kaufman et al.

(10) Patent No.: US 7,209,779 B2
(45) Date of Patent: Apr. 24, 2007

(54) METHODS AND SOFTWARE FOR RETROSPECTIVELY GATING A SET OF IMAGES

(75) Inventors: Leon Kaufman, San Francisco, CA (US); Freiderike Griess, Santa Clara, CA (US)

(73) Assignee: Accuimage Diagnostics Corp., So. San Francisco, CA (US)

( * ) Notice: Subject to any disclaimer, the term of this patent is extended or adjusted under 35 U.S.C. 154(b) by 964 days.

(21) Appl. No.: 10/159,814

(22) Filed: May 30, 2002

(65) Prior Publication Data

US 2003/0016852 A1 Jan. 23, 2003

Related U.S. Application Data

(60) Provisional application No. 60/306,311, filed on Jul. 17, 2001.

(51) Int. Cl.
*A61B 5/05* (2006.01)
(52) U.S. Cl. .................. 600/425; 600/500; 600/521; 378/165
(58) Field of Classification Search .............. 378/8, 378/165; 600/425, 500, 521
See application file for complete search history.

(56) References Cited

U.S. PATENT DOCUMENTS

| | | |
|---|---|---|
| 3,916,877 A | 11/1975 | Beckman |
| 3,954,098 A | 5/1976 | Dick et al. |
| 4,454,610 A | 6/1984 | Sziklai |
| 4,590,558 A | 5/1986 | Glover et al. |
| 4,908,573 A | 3/1990 | Kaufman et al. |
| 5,036,281 A | 7/1991 | Li |
| 5,119,816 A | 6/1992 | Gevins |
| 5,271,055 A | 12/1993 | Hsieh et al. |
| 5,431,161 A | 7/1995 | Ryals et al. |
| 5,570,404 A | 10/1996 | Liang et al. |

(Continued)

OTHER PUBLICATIONS

Kramer, D. et al., "Applications of Voxel Shifting in Magnetic Rosonance Imaging," Toshiba America MRI, and University of California, San Francisco, Radiologic Imaging Laboratory, South San Francisco, CA, vol. 25, No. 12, pp. 1305-1310.

(Continued)

*Primary Examiner*—Brian L. Casler
*Assistant Examiner*—Jacqueline Cheng
(74) *Attorney, Agent, or Firm*—Townsend and Townsend and Crew LLP

(57) ABSTRACT

Methods, devices, and software for selecting image slices. The image slices are preferably taken during a quiet part of the patient's heart cycle in which the heart is relatively motionless so as to reduce blurring and the introduction of artifacts into the resultant reconstructed projection image of the heart. The methods of the present invention can analyze information regarding the duration of the patient's R-R cycles and allow the user to choose from a plurality of selection criteria, typically an absolute time or a percentage of the R-R cycle, so as to select slice images for inclusion in a projection image. The ability to choose from a plurality of selection criteria provides for flexibility to account for irregular heartbeats or a change in the duration of the patient's R-R cycles. In exemplary embodiments, the resultant projection image can be used for coronary calcium scoring or 3-D rendering of the heart.

6 Claims, 11 Drawing Sheets

U.S. PATENT DOCUMENTS

| | | | |
|---|---|---|---|
| 5,734,882 A | 3/1998 | Lopresti et al. | |
| 5,986,662 A | 11/1999 | Argiro et al. | |
| 6,023,635 A * | 2/2000 | Liu et al. | 600/410 |
| 6,211,674 B1 * | 4/2001 | Cline et al. | 324/307 |
| 6,226,352 B1 | 5/2001 | Salb | |
| 6,233,478 B1 | 5/2001 | Liu | |
| 6,243,437 B1 | 6/2001 | Hu et al. | |
| 6,252,924 B1 | 6/2001 | Davantes et al. | |
| 6,317,617 B1 | 11/2001 | Gilhuijs et al. | |
| 6,353,653 B1 | 3/2002 | Edic | |
| 6,370,217 B1 | 4/2002 | Hu et al. | |
| 6,421,552 B1 | 7/2002 | Hsieh | |
| 6,426,987 B2 | 7/2002 | Nakamura et al. | |
| 6,473,634 B1 | 10/2002 | Barni | |
| 6,484,048 B1 * | 11/2002 | Hoshino et al. | 600/410 |
| 6,504,893 B1 | 1/2003 | Flohr et al. | |
| 6,504,894 B2 | 1/2003 | Pan et al. | |
| 6,522,712 B1 | 2/2003 | Yavuz et al. | |
| 6,526,117 B1 | 2/2003 | Okerland et al. | |
| 6,535,570 B2 | 3/2003 | Stergiopoulos et al. | |
| 6,539,074 B1 | 3/2003 | Yavuz et al. | |
| 6,560,309 B1 * | 5/2003 | Becker et al. | 378/8 |
| 6,563,941 B1 | 5/2003 | O'Donnell et al. | |
| 6,584,216 B1 | 6/2003 | Nyul et al. | |
| 6,603,494 B1 * | 8/2003 | Banks et al. | 715/807 |
| 6,687,393 B1 | 2/2004 | Skinner, Jr. | |
| 6,728,566 B1 | 4/2004 | Subramanyan et al. | |
| 6,765,983 B2 | 7/2004 | Yan et al. | |
| 6,879,656 B2 | 4/2005 | Cesmeli et al. | |
| 6,901,277 B2 | 5/2005 | Kaufman et al. | |
| 6,928,314 B1 * | 8/2005 | Johnson et al. | 600/407 |
| 7,006,862 B2 * | 2/2006 | Kaufman et al. | 600/523 |
| 2003/0013953 A1 * | 1/2003 | Mistretta | 600/425 |
| 2003/0016782 A1 | 1/2003 | Kaufman et al. | |
| 2003/0016851 A1 | 1/2003 | Kaufman et al. | |
| 2003/0018251 A1 | 1/2003 | Solomon | |
| 2004/0042581 A1 | 3/2004 | Okerland et al. | |
| 2004/0077941 A1 | 4/2004 | Reddy et al. | |

OTHER PUBLICATIONS

Press Release, "Vital Images Releases Viteca(R)2 Version 2.2 and VScore™ With AutoGa," Feb. 22, 2001, pp. 1-3 downloaded Sep. 18, 2005 from http://phx.corporate-ir.net/phoenix.zhtml?c=108290&p=irol-newsArticle&ID-154387&highl....

Brejl et al., "Retrospective Gating of Cardiac CT Images without EKG Signals," *Radiology (Positioning)*, vol. 453, abstract only (2001).

Hong et al., "ECG-gated Reconstructed Multi-Detector Row CT Coronary Angiography: Effect of Varying Trigger Delay on Image Quality," *Radiology*, 220(3):712-717 (2001).

Kopp et al., "Coronary Arteries: Retrospectively ECG-gated Multi-Detector Row CT Angiography with Selective Optimization of the Image Reconstruction Window," *Radiology*, 221(3):683-688 (2001).

Mao et al., "Effect of Electrocardiogram Triggering on Reproducibility of Coronary Artery Calcium Scoring," *Radiology*, 220(3):707-711 (2001).

Product Brochure for VScore™ A Vitrea® 2 Option, pp. 1-2, downloaded from file://C:\DOCUME~1\SKB\LOCALS~1\Temp\SD1WERGQ.htm on Jul. 15, 2005, and Chapter 2, pp. 2-1 through 2-15, "Learning VScore with Gating Options," and Chapter 3, pp. 3-1 through 3-9, "Using VScore with Gating Options," from Users Manual for VScore™ product.

* cited by examiner

FIGURE 12
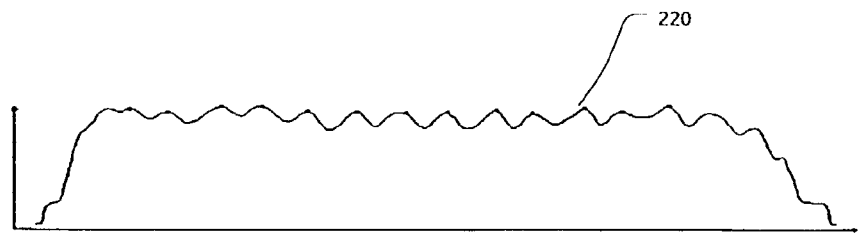
FIGURE 13
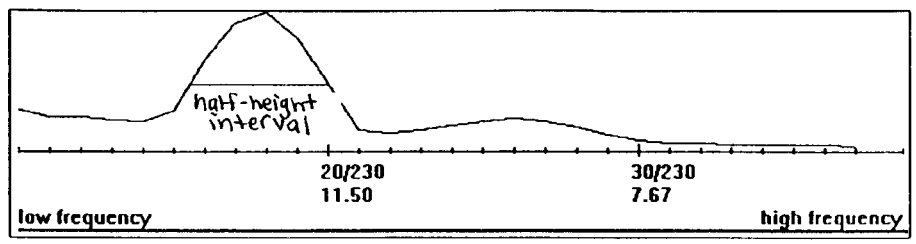
FIGURE 14
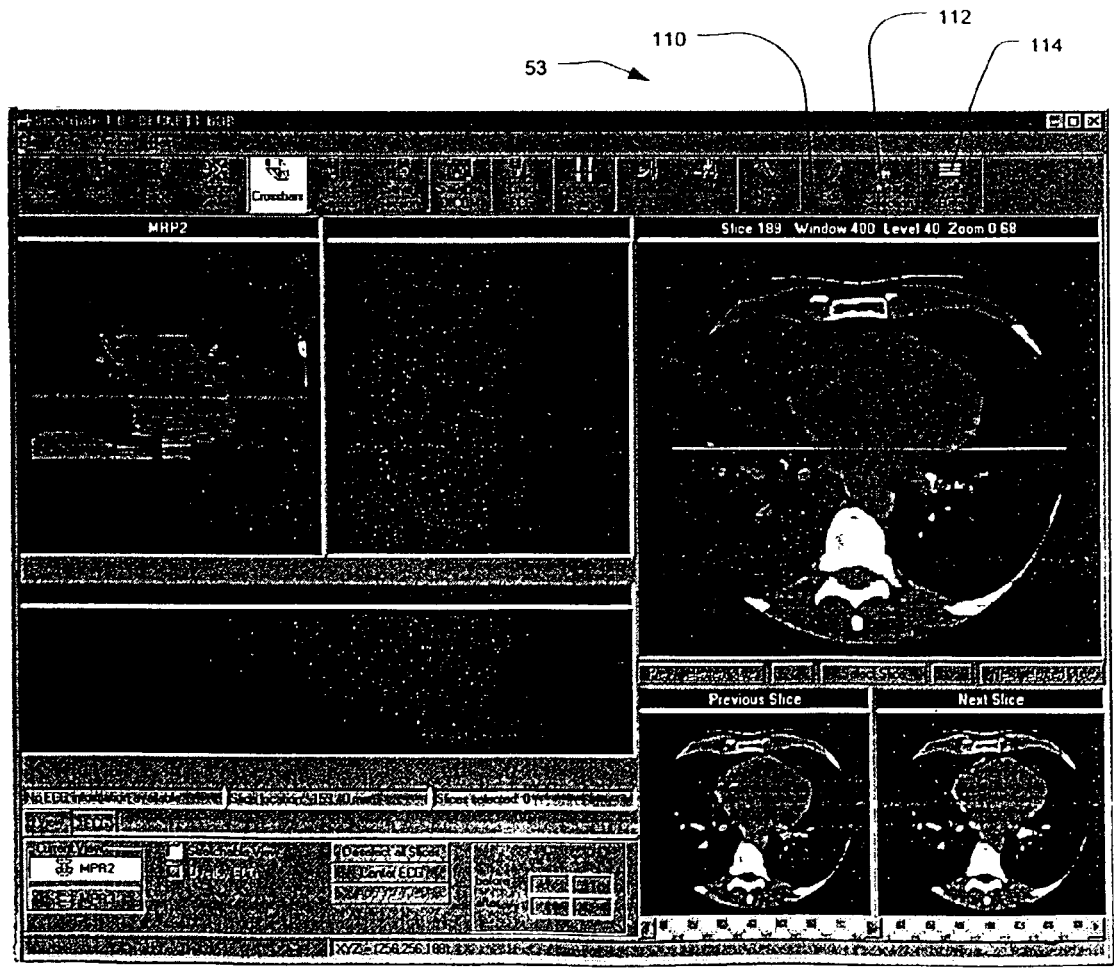
FIGURE 15

METHODS AND SOFTWARE FOR RETROSPECTIVELY GATING A SET OF IMAGES

CROSS-REFERENCE TO RELATED APPLICATIONS

The present application claims benefit to U.S. Provisional Patent Application Ser. No. 60/306,311 filed Jul. 17, 2001, the complete disclosure of which is incorporated herein by reference.

The present application is also related to U.S. Patent Application entitled "Graphical User Interfaces and Methods for Retrospectively Gating a Set of Images" filed herewith, application Ser. No. 10/159,816 and U.S. Patent Application entitled "Methods and Software for Self-Gating a Set of Images," also filed herewith, application Ser. No. 10/159,813, the complete disclosures of which are incorporated herein by reference.

BACKGROUND OF THE INVENTION

The present invention relates generally to medical imaging. More specifically, the present invention relates to gating of an image scan to improve calcium scoring of a patient's heart and coronary arteries.

CT scanning of the heart is an increasingly common procedure to obtain information about the presence of calcification in the coronary arteries. Unfortunately, two body motions can interfere with the quality of the images obtained by the CT scanner: the heart motion and the patient's breathing motion. A normal heart scan takes about 20 seconds and to reduce the effect of the breathing motion, the patient is generally asked to hold their breath to eliminate the breath motion. The heart motion, on the other hand, cannot be readily eliminated and can lead to blurring, introduction of artifacts into the images, and misregistration.

A common procedure to reduce the heart motion is gating. As is described in U.S. Pat. Nos. 6,370,217 B1 and 6,243,437 to Hu et al., the motion of the heart is fastest during systole and relatively motionless during diastole. Prospective gating methodologies use an electrocardiograph signal (ECG) to predict the time of the diastole such that the CT scanner can be activated to obtain an image during the relatively motionless diastole period. A major issue with prospective gating in subjects with irregular heart beats is that the trigger can only be set to acquire data after the R-wave. If the following beat is short, the data acquisition may overlap the next systolic period. Retrospective gating, on the other hand, uses the electrocardiograph signal to retrospectively find motionless points in the heart cycle to select the image slice. In retrospective gating, the ECG signal information can be used, in retrospect, to select the slice images that were acquired during the diastole. The heart moves through a cycle in somewhat under a second, and a scanners generally take from a quarter second to a half second to acquire the information for each slice, thus it is possible to select from a number of slices for each cardiac cycle.

There are two major issues with retrospective gating. The first is that while reconstruction at finer intervals than the whole acquisition cycle does not increase the radiation dose to the subject to produce the extra images, the overlap of the scanned volume and the fact that the scanner's x-ray tube is continuously on (instead of being turned off during the parts of the cardiac cycle that are not of interest) increase the radiation dosage. The second problem is that gating from an ECG signal requires the placement of electrodes on the subject and testing to confirm that their placement is adequate. In a busy screening or diagnostic practice the added steps can decrease utilization and negatively affect the economics of the imaging operation.

There are various shortcomings in existing software for retrospective gating. When the operator is performing the selection of slices, there is no real time feedback as to the adequacy of the selection. Information as to the length of the cardiac cycle during the study, convenient ways to ascertain whether it changed during the study, and measurement of any one cycle are also not readily available. Except for manually adjusting each slice (there can be 350–500 slices in a study), there is no way to account for changes in the cardiac cycle. All of these contribute to decreasing the certainty with which a particular coronary calcium score is known, and to increasing the variability of the resulting calcium scores.

Consequently, what is needed are improved methods and software for generating a reconstructed projection image of the patient's heart which more fully utilizes the information content of the acquisition cycle, so that less of the increased dose is wasted or thrown out. Additionally, what is also needed are methods and software that can gate an image scan without the use of an ECG signal.

BRIEF SUMMARY OF THE INVENTION

The present invention provides methods, software, and computer systems for gating images of the patient's heart.

In particular, the present invention retrospectively gates a set of image slices by analyzing the duration of the patient's R-R cycles and selecting a subset of slices based on the duration and change in the duration (if any) of the patient's R-R cycles. Preferably, the chosen subset of images are obtained during a diastole of the patient's heart cycle.

Exemplary methods of the present invention are used to image a patient's heart. The resultant image from the methods of the present invention can be used for calcium scoring, 3-D rendering, or the like.

Determination of a time point relative to the R-wave is an important factor for image quality and for reliable diagnostic results. Images acquired during a diastole, in which the heart is fully expanded and relatively motionless, provide the clearest images of the heart. Because the heart cycle of the patient may change during the acquisition of the images or because the patient may have an irregular heartbeat, the present invention allows for a flexible selection of the time point during the R-R cycle in which the image slice is selected.

In some embodiments, the present invention provides a graphical illustration of the duration of the R-R cycle over the acquisition time period. The graph can provide the user with a visual indication as to the presence of any changes in the duration of the R-R cycle. Additionally or alternatively, the present invention can calculate and display numerical information regarding the duration of the R-R cycle for different periods of the acquisition period. For example, the numerical information can illustrate the duration and change of duration of the R-R cycle for the first 10 cycles, the middle 10 cycles, and the last 10 cycles.

The information regarding the duration of the R-R cycle can inform the user if the patient has an irregular heartbeat or if there is a change in the duration of the R-R cycle over the acquisition period. With this information, the user will be given the option of choosing a selection criteria that is appropriate for the measured R-R cycle duration.

In exemplary embodiments, the user will be given the option of selecting from a plurality of selection criteria. One exemplary selection criteria is an absolute time (before or after) the R-wave. Another exemplary selection criteria is a percentage of the R-R cycle (before or after) the R-wave.

After the selection criteria has been chosen and applied to the set of image slices, a subset of the image slices will be chosen. A coronal or sagittal projection image can thereafter by generated using the subset of images that were chosen with the selection criteria. The invention of this application is not limited to the use of coronal or sagittal projections. Other projections may be chosen, such as those of the heart's short or long axis.

If any of the selected slices are deemed to be not appropriate for the projection image, the user can scroll through the selected (and deselected) slices to choose more appropriate slices for inclusion in the projection image. Advantageously, the user can be provided with an image of the generated projection coronal/sagittal projection image alongside the projection image that includes all of the overlapping slices of the image set. Moreover, the projection image with the selected slices can be updated in real time so as to show the user the effect of the added slice(s).

In one specific embodiment, the present invention provides a method of retrospectively gating an image scan. The method comprises acquiring a plurality of overlapping slice images of a volume of tissue of a patient. An ECG signal of the patient is measured and a duration of each of the patient's R-R cycles is calculated. The user can choose from a plurality of slice selection criteria based on the duration of the patient's R cycle and slices are selected from the image scan using the slice selection criteria. Thereafter, a reconstruction of the volume of tissue of the patient is regenerated using the selected slices.

In another particular embodiment, the method of the present invention provides a method of generating an image of a patient's heart. The method includes acquiring a plurality of overlapping slice images of the patient's heart. A duration of each cardiac cycle is measured. Slice images for inclusion into a reconstruction (e.g., coronal or sagittal projection) are selected based on the measurement of the duration of the cardiac cycle.

The duration of the R-R cycle can be analyzed to see if there are any changes in the duration. If the duration of the R-R cycle is relatively consistent throughout the acquisition period, a selection criteria of an absolute time can be used to select the slices. If, however, the duration information shows that there is a change over the acquisition period, the selection criteria of a percentage of the R-R cycle can be chosen.

In another embodiment, the present invention provides a method of selecting slices from an image scan. The method comprises acquiring a plurality of overlapping slice images of a patient and an ECG signal of the patient. A first set of slice images from the plurality of overlapping slice images are chosen based on the timing relative to the ECG signal. A maximum intensity projection algorithm is applied to each slice of the first set of slices and slices immediately adjacent the slices in the first set to generate a maximum intensity projection slice that contains, on a pixel by pixel basis, information from a pixel with the highest intensity in the three slices. A second set of slices is generated from the maximum intensity projection slices.

For a further understanding of the nature and advantages of the invention, reference should be made to the following description taken in conjunction with the accompanying drawings and claims.

BRIEF DESCRIPTION OF THE DRAWINGS

FIG. 12 is an example of an intensity profile;

FIG. 13 is a smoothed output of a local intensity signal with markers indicating maxima obtained from a derivative filter;

FIG. 14 is an example of a power spectrum;

FIG. 15 illustrates a graphical user interface in which an ECG has not been loaded and a user can self-gate the image scan;

DETAILED DESCRIPTION OF THE INVENTION

The present invention provides methods and graphical user interfaces for self gating and retrospectively gating a set of image slices (referred to herein as an image scan).

While the remaining discussion focuses on the gating of an image scan from a CT scanner for use in coronary calcium measurements, it should be appreciated that the methods and devices of the present invention are not limited to such imaging modalities and uses. For example, instead of analyzing the image scan for measuring coronary calcium, the image scan can be used for 3-D reconstructions of the heart, such as those used for CT angiography, or for heart function studies, including dynamic studies.

In some exemplary embodiments, the present invention uses a patient's measured ECG signals taken during the acquisition of the image scan to gate the image scan. The ECG signal is a repetitive pattern that reflects the electrical activity of the patient's heart. An ECG signal has a plurality of cardiac cycles (sometimes referred to as R-R cycles), with each cardiac cycle beginning with an R-wave (e.g., highest amplitude peak) during a systole period and ending with a relatively motionless diastole period. Blurring of the images is most likely to occur when imaging during systole. Consequently, it is preferable to use image slices taken during the diastole period so as to reduce the amount of artifacts introduced into the reconstruction image(s).

Unfortunately, the R-R interval can vary through the image scan and the cardiac cycle will not always occur at regular intervals (e.g., irregular heartbeat). For example, in many imaging sessions, the subject is asked to hold their breath so as to reduce introduction of artifacts due to the breathing motion. The patient's holding of their breath, however, may cause a change in the heart cycle. Additionally, patient's who have irregular heart beats may not be effectively imaged by selecting a specific point in time during the cardiac cycle. While some studies have proclaimed that it is best to select a particular time with respect to the R-wave, (some preferring a certain number of milliseconds before or after the R-wave), the selection of an absolute time does not allow for compensation for irregular heartbeats or changing times between successive R-waves.

Figure 1:
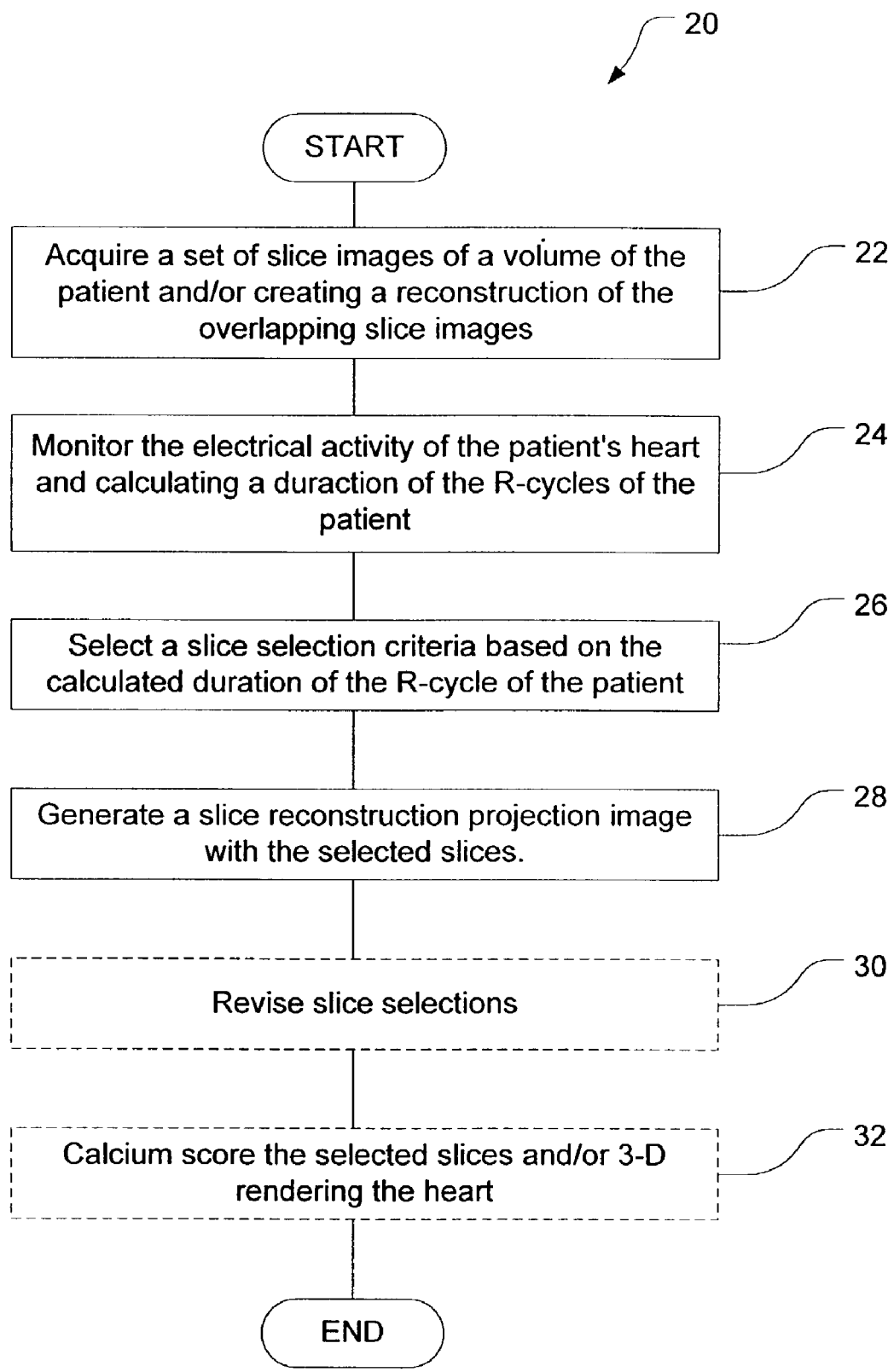
FIG. 1 schematically illustrates a simplified retrospective gating method of the present invention with the optional steps in dotted lines.

FIG. 1 schematically illustrates one method 20 of the present invention. First, a set of slice images of a volume of tissue of the patient is obtained and a coronal or sagittal reconstruction of the slice images can be generated. (Step 22). Acquisition of the image scan can be carried out by any conventional or proprietary CT scanner (e.g., moving, stationary, single detector, multiple detector, helical, and the like). A helical scan of the heart can include approximately 350–500 overlapping images, while a non-overlapping scan usually includes around 40–50 slices. It should be appreciated however, that it may be possible to use magnetic resonance image (MRI) scanners, ultrasound scanners, or other slice imaging devices to obtain the image scan used in the methods of the present invention.

The electrical activity of the patient's heart can be measured by attaching one or more electrocardiograph leads to the patient to monitor the patient's ECG signal during the acquisition of the image scan. The electrical activity can be analyzed to derive information regarding the duration of each of the R-R cycles of the ECG signal (Step 24). The R-R cycle information allows the user to determine if there are any substantial variations in the duration of the R-R cycles over the acquisition period of the slice images. Such information allows the user to make appropriate adjustments to their selection of the slice images used for generating the coronal/sagittal projection for calcium scoring, or for 3-D rendering.

Figure 2:
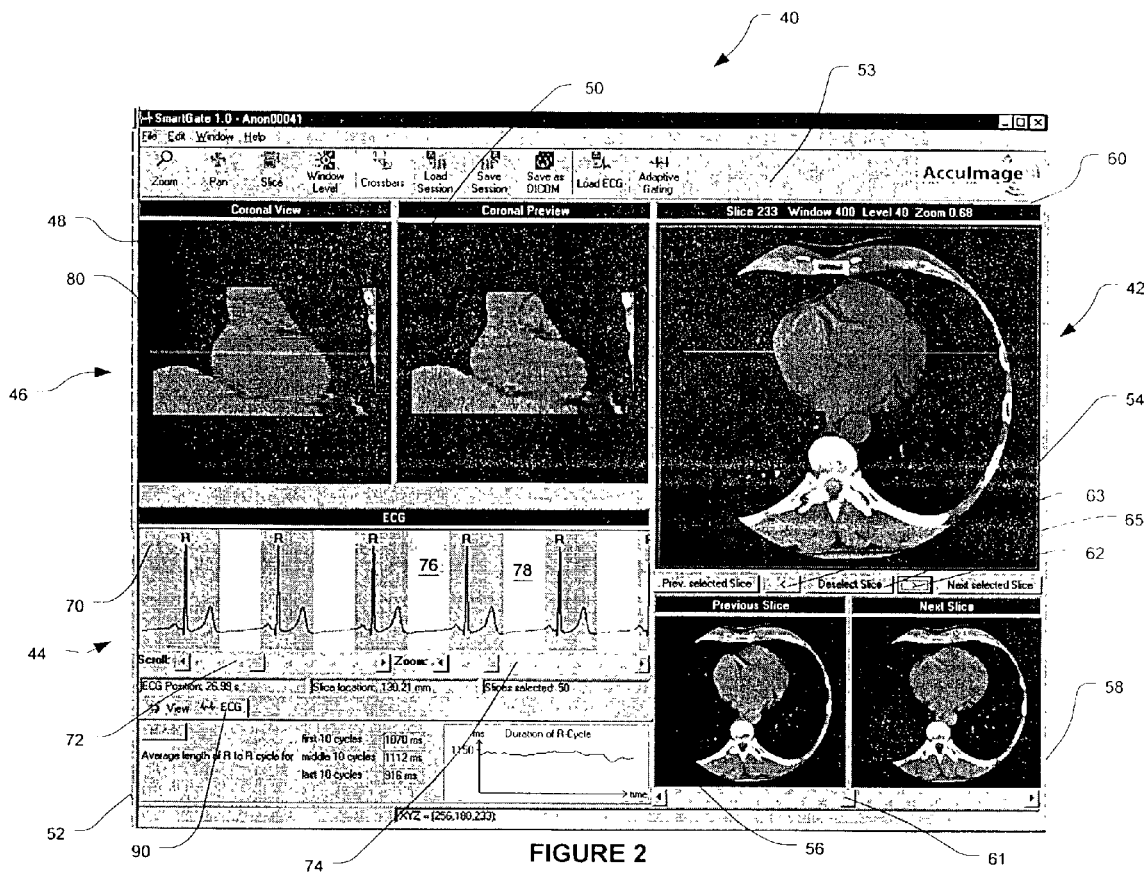
FIG. 2 illustrates one exemplary graphical user interface displaying information regarding the duration of an R-R cycle of a patient.
Figure 3:
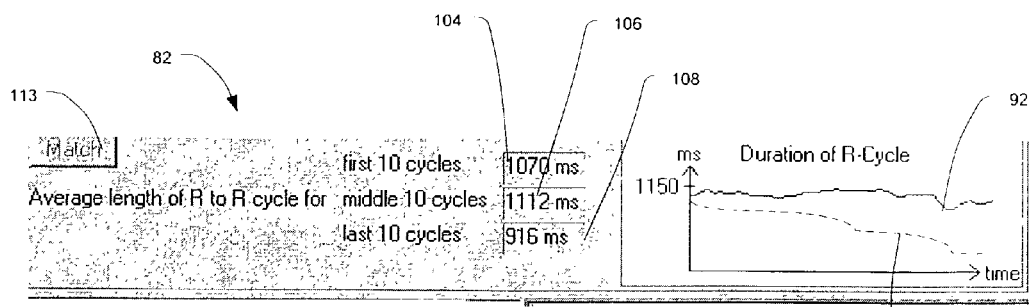
FIG. 3 is an enlarged portion of the R-R cycle information of FIG. 2.

The ECG information can be analyzed automatically by software or manually by the user to determine the duration of each cardiac cycle (illustrated in FIGS. 2 and 3 as "Duration of R-Cycle"). Based on the calculated R-R cycle information, the user can choose an appropriate global selection criteria of choosing the slice images from the image scan (Step 26). In exemplary embodiments, the selection criteria for choosing the slice image(s) includes (1) an absolute time period before or after the R-wave or (2) a percentage of the cycle (e.g., 65% of the heart cycle) before or after the R-wave. In exemplary embodiments, the user will be allowed to separately choose the selection criteria (e.g., percentage or absolute time) and a timing selection (e.g., before or after the R-wave).

It should be appreciated however, that while the preferred selection criteria are an absolute time before or after the R-wave or a percentage of the cardiac cycle before or after the R-wave, that other selection criteria may be used to select the slice images.

In some embodiments, when the user selects a percentage of the cycle as the selection criteria, the software of the present invention can also display a complementary time value that corresponds to the selected percentage. Similarly, if a user chooses an absolute time period, the software of the present invention can display the corresponding percentage. This significantly decreases operator load. For instance, for most of the heart cycles, the heart rate may be quite constant. The operator can set a preferred time, say, 450 msec before the R-wave, and the program will show what percentage of the cycle this is. The operator can then select for a portion of the scan when the heart rate slows near the end, a percentage that is already available from the software. In another case the heart rate may have increased, and the end of the scan may overlap the following R-wave. The operator can then select the complementary time after the R-wave to better center the selected image.

In exemplary embodiments, a graphical illustration of the duration of the R-R cycle can be displayed on a user interface to illustrate the duration of the R-R cycle. Advantageously, the graph of the R-R cycle will guide the user toward the patient's irregular heart beats and show if there are any substantial variations in the length of the R-R cycle that may effect the selection of the slices.

One example of a graphical illustration is illustrated in FIG. 3. Graph 92 shows that the duration of the R-R cycle is substantially the same length during the entire acquisition period. Graph 94 (in dotted lines) shows that the duration of the R-R cycle changes over the acquisition period.

In the instance in which graph 92 is relatively consistent over time, the user can apply an absolute time period (before or after the R-wave) to select the slice images for inclusion in the reconstruction projection image. Since the R-R cycles are substantially the same throughout the acquisition period, the absolute time period should generally fit each of the R-R cycles.

If the duration of the R-R cycle changes over the acquisition period (shown as a dotted line 94), the user would likely use the "percentage of cardiac cycle" (before or after the R-wave) selection criteria to select the slices since the absolute time does not compensate for irregular or changing times of the R-R cycle. While an absolute time period, (for example 450 msec before the R-wave) may be appropriate for a first portion of the ECG signal, because the R-R cycle decreases over time, the chosen absolute time period would likely be inappropriate for the latter, shorter R-R cycles since the selected slice would likely overlap over a portion of the high amplitude R-wave. Thus, such a slice would likely introduce artifacts into the resultant projection image and reduce the accuracy of the calcium scoring of the image slice.

Additionally or alternatively, to graphically illustrate the duration of the R-R cycle, the methods of the present invention can also numerically display the duration of the R-R cycle for specific intervals of the acquisition period of the ECG. For example, as illustrated in FIG. 3, the acquisition period may be broken up into a plurality of intervals. In one exemplary embodiment, the first interval 104 is the first 10 cycles of ECG, the second interval 106 is the middle 10 cycles of the ECG, and the third interval 108 is the last 10 cycles of the ECG. It should be appreciated however, that the ECG can be separate into any number of different ECG intervals, and the present invention should not be limited to the illustrated three intervals.

By quantitatively providing the average length of the R-R cycle for the different intervals, the user will be able to accurately determine which selection criteria to employ. For example, if the R-R cycle duration varies by more than a certain percentage or time length (typically about 70 msec or about 10% of the R-R cycle), the user will likely want to employ the percentage selection criteria. But if the R-R cycle duration difference is less than the certain percentage or time length, the user will likely want to employ the absolute difference criteria, as described above.

Alternatively, instead of choosing a global absolute time period for all of the cycles, it may be possible to apply a separate selection criteria to each of the intervals of the ECG. Thus, if two of the intervals are consistent and the third interval is changing in duration or at a lower duration than the first two intervals, it may be beneficial to apply an absolute time selection criteria to the first two intervals and a shorter absolute time duration or a percentage of cycle to the third interval. For example, for the illustrated example in FIG. 3, as first attempt, the user can select a slice image that is 450 msec before the R-wave for first 10 cycles, 450 msec before the R-wave for middle 10 cycles, and 400 msec before the R-wave for last 10 cycles. In this manner, an optimal selection can be achieved, the possibilities being limited by the acquisition process, and not the gating software.

After the appropriate selection method is chosen and applied, the selected slices will be combined to generate a corrected coronal/sagittal projection. (Step 28). In some embodiments a bilinear algorithm is used to generate the correct aspect ratio coronal/sagittal projection. It should be appreciated however, that other conventional interpolation and scaling algorithms can be used.

The combination of functionalities and flexibility in choosing the slices allow for convenient and at the same time highly specific selection of slices on the basis of timing with respect to the ECG signal. Because the selection of the slices can be displayed to the user in real time (described below), the user can rapidly assess the adequacy of the timing selection of the slice images.

If the projection images are deemed to be acceptable, the selected slices can be calcium scored or 3-D rendered, if desired. (Step 32). Because there is an overlap of the slices during scanning, and because the x-ray tube is on during the full cardiac cycle instead of just during the acquisition of the desired time interval within the cycle (as in prospective gating) there is an increase in delivered radiation dose to the patient. Such a dosage increase in unavoidable, but retrospectively it is possible to obtain information from the additional radiation dose. After acquisition, the reconstruction software can generate additional slices at finer intervals than those determined by table motion and scanner rotation speed, typically ten times finer. In methods which analyze the slice images for calcium scoring, the calcium will be very bright in the images. Using a maximum intensity projection algorithm, the selected slice and its two immediate neighbors can be analyzed to select the brightest pixel in each of the slices. The slice that has the brightest pixel can then be chosen for inclusion in the calcium scoring study. Thus, the process of the present invention effectively utilizes three out of ten images (e.g., the "selected" slice and its two neighbors) instead of just one out of every ten images.

Because a CT image is obtained from hundreds of individual projections and processed through back-projection algorithms, inconsistencies in some projections due to heart motion or motion of a point in the heart that in some way aliases with the acquisition process can produce a significant artifact even at a time where the heart is relatively quiescent. Optionally, if the selected slice images chosen by the above method are not all deemed appropriate because of such a problem, the user can manually scroll through the selected slice images and choose other "non-selected" slice images to replace the undesired "selected" slice images. (Step 30). One method of deselecting slices from the image scan is described below, in relation to one exemplary graphical user interface of the present invention.

FIGS. 2–6 illustrate some exemplary graphical user interfaces and methods for gating an image scan. It should be appreciated however, that the graphical user interfaces described and illustrated herein are meant only to be examples, and should not be used to limit the scope of the present invention.

FIG. 2 schematically illustrates one exemplary graphical user interface (GUI) 40 of the present invention. GUI 40 is generally displayed on a user output device such as a computer monitor. GUI includes a first screen portion 42 for displaying a selected image, a second screen portion 44 for displaying an ECG that was taken during the image scan, and a third screen portion 46 for displaying a coronal and/or a sagittal image projection of the selected slices. Typically, third screen portion 46 will display a first projection image 48 that is composed of all of the slices of the image scan and/or a second projection image 50 that is composed only of the selected images slices. As will be described in detail below, GUI can further include a fourth screen portion 52 that can be toggled between a variety of views to allow a user to select and display various functions, menus, and information. GUI can also include a menu toolbar 53 so as to allow a user to select and toggle between the different functionalities and plug-ins of the software of the present invention.

In preferred embodiments the GUI 40 of the present invention can simultaneously display on a single screen a selected slice image, at least a portion of the ECG signal, and the sagittal/coronal reconstruction projection image that is composed of the selected slices. Such an interface 40 allows the user to view in real-time, the effect that the choice or change of image slices has on the quality and resolution of the composite projection image. Thus, if the selected slices do not improve the quality of the coronal or sagittal reconstruction projection image, the user can de-select the slice(s) to improve the image quality, and hence improve the calcium scoring or 3-D rendering of the patient's heart.

As shown in FIG. 2 in exemplary embodiments first screen portion 42 can display a selected slice image in window 54 and previous and next slice images in windows 56, 58, respectively. Slice image window 54 can include a header 60 that indicates the slice number, zoom level, and the like. The adjacent slice image windows 56, 58 can include a header that indicates "Previous Slice" or "Next Slice." It should be appreciated however, that a variety of headers can be used to indicate other information, if desired. Image windows 56, 58 can include a scroll bar 61 that allows a user to scroll through (review) the slice. In some exemplary embodiments, image windows 56, 58 that display the non-selected slices are smaller in size than image window 54. It should be appreciated however, that if desired, image windows 56, 58 can be the same size or larger than image window 54 if desired.

First screen portion 42 can also include user actuatable buttons 62, 63 that allows the user to toggle through the other individual slice images of the image scan. If user actuates button 63, the image slice that was originally displayed in window 58 will be displayed in window 54, the image slice that was originally displayed in window 54 will be moved to image window 56, the image originally displayed in image window 56 will not be displayed, and a previously undisplayed slice image will be shown in window 58. Likewise, if a user actuates button 62, the image slice that was originally displayed in window 56 will be displayed in window 54, the image slice that was originally displayed in window 54 will be moved to image window 58, the image originally displayed in image window 58 will not be displayed, and a previously undisplayed slice image will be displayed in window 56.

Figure 4:
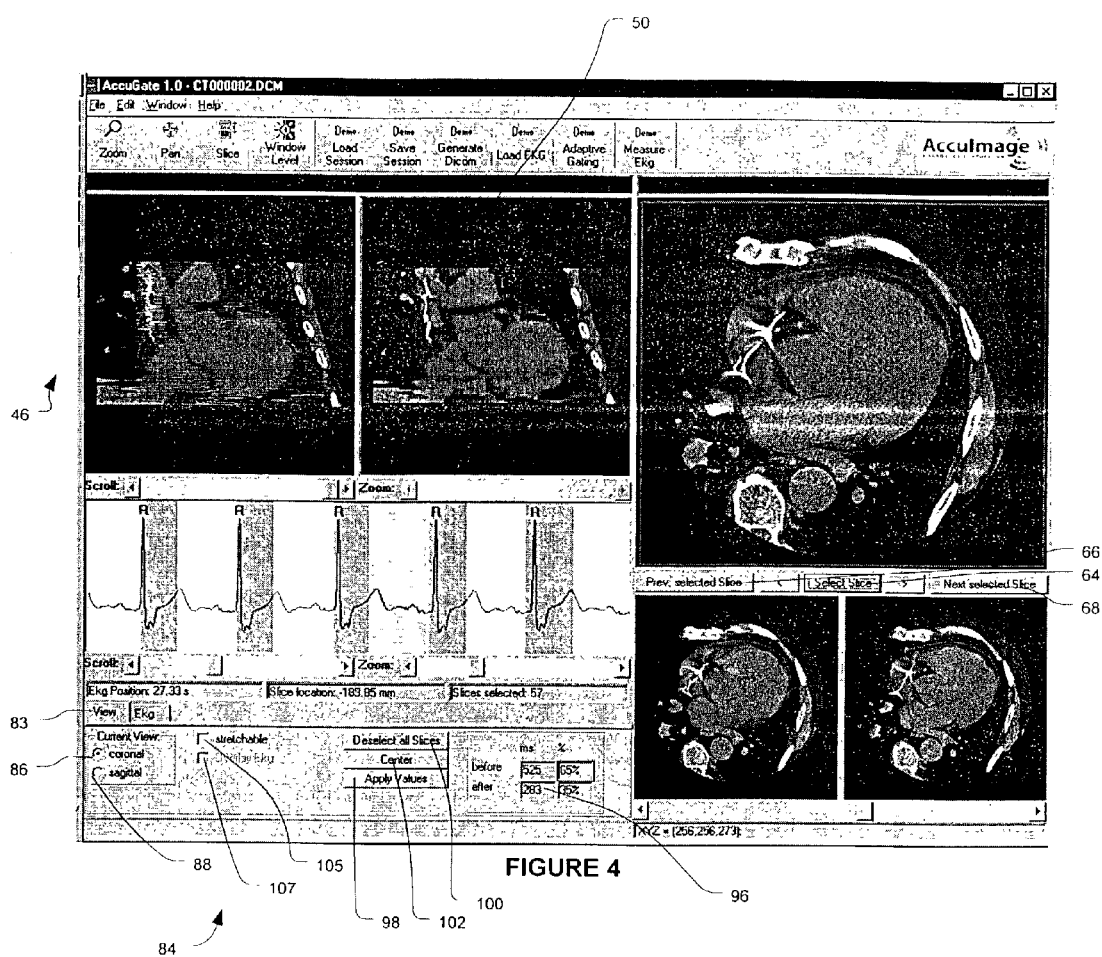
FIG. 4 illustrates a graphical user interface having the view tab and view screen displayed and slice images selected during a diastole.

As shown in FIG. 4, if the slice image displayed in window 54 is not a "selected slice," first screen portion 42 can include a "Select Slice" button 64 that allows the user to select a previously "unselected" slice that is displayed in window 54 for inclusion into the projection image displayed in third screen portion 46. Similarly, if a slice displayed in window 54 is a slice that is already selected or included in projection image 50, first portion 42 can include a "Deselect" button 65 that, when actuated, can remove the slice from inclusion in the reconstruction projection image. (FIG. 2)

If through any of the process described therein, there are gaps in the image data, before saving or calcium scoring the gated image, the user will be warned of the gaps and asked if the gaps should be filled. If the user chooses to fill the gap, the software can automatically fill the gap by selecting a slice image that is substantially in the middle of the gap.

As shown in FIG. 4, in exemplary embodiments, first portion 42 can also include a "Previously Selected Slice" button 66 and a "Next Selected Slice" button 68 that allows the user to jump to the next or previous selected slice in the image scan. In exemplary embodiments, the next selected slice will be a slice that corresponds to a similar time point during the R-R cycle, as described above.

Windows 48, 50, 54, 56, 58 can be zoomed in and out, panned to adjust the size of the image displayed. The zooming and panning can be done synchronously for all of the windows, or the zooming of each window can be performed independent of each other.

Referring again to FIG. 2, second screen portion 44 of GUI 40 can include an ECG field 70 that displays a patient's ECG signal that was taken during the imaging of the patient's heart. In most embodiments, only a portion of the entire ECG reading will be displayed on the screen. Thus, a scroll bar 72 and a zoom bar 74 can allow the user to scroll through the ECG and/or to zoom in and out of the ECG.

The ECG field can be highlighted, typically through a difference in colors or shading from a background of the ECG field, to indicate which slices are chosen relative to the ECG for inclusion into the projection image 50. For ease of reference, the selected slice image that is displayed in window 54 will generally have a different shading from the ECG field background and the highlighting of the other selected slices. In one exemplary embodiment, the slice displayed in window 54 will be identified in the ECG field by a light red band 76, and the other selected slices will be identified by a blue band 78.

In some embodiments, if the user wishes to manually measure the time interval of an R-R cycle(s), the user can measure the time interval between two arbitrary or chosen points within the ECG setting one boundary delimiter by clicking into the ECG and dragging the free boundary delimiter with a mouse, or other input device, to the second point on the ECG. A field below the ECG can then display the time length between the two selected points (not shown).

As seen further in FIGS. 2, 4, and 5, information regarding the number of selected slices, position of the current slice in the ECG (in milliseconds), and the position of the current slice in millimeters, can be placed below the ECG field to provide information to the user about the selected slice and ECG.

As the user scrolls through images in the first portion 42, the user can merely click on the image window 54 to center the ECG cardiac cycle within the ECG field so that the user can simultaneously view the selected image slice and its corresponding cardiac cycle. Alternatively clicking on a portion of a stretched (or normal) reconstruction projection will display such a slice in window 54 and center the corresponding ECG signal in the ECG field. Moreover, the user can use scrollbar 72 below the ECG field to scroll through the R-R cycles until the selected R-R cycle is displayed within the ECG field. As noted, the selected R-R cycle will be highlighted a different color from the other selected R-R cycle slices. Also, clicking on the ECG display will select a slice with its center closest to the point where the user had placed a cursor. The slice will be highlighted on the ECG to display the location of the slice relative to the ECG.

Third screen portion 46 can be configured and sized to display one or more reconstruction projection images. In exemplary embodiments, third screen portion 46 can display a coronal and a sagittal projection image of the slices. Alternatively, third screen portion 46 can display only a projection image that is composed of only the selected slices. If desired, in order to provide a visual impression of the image quality of the projection image with only the selected slices 50, a projection image having all of the slice image of the image scan 48 can be shown adjacent image 50. Additionally, the third screen portion may only show the coronal/sagittal projection image having only the selected slices.

Third portion 46 can include a line 80 across the reconstruction projection image to indicate the position of the slice image that is displayed in window 54.

Figure 5:
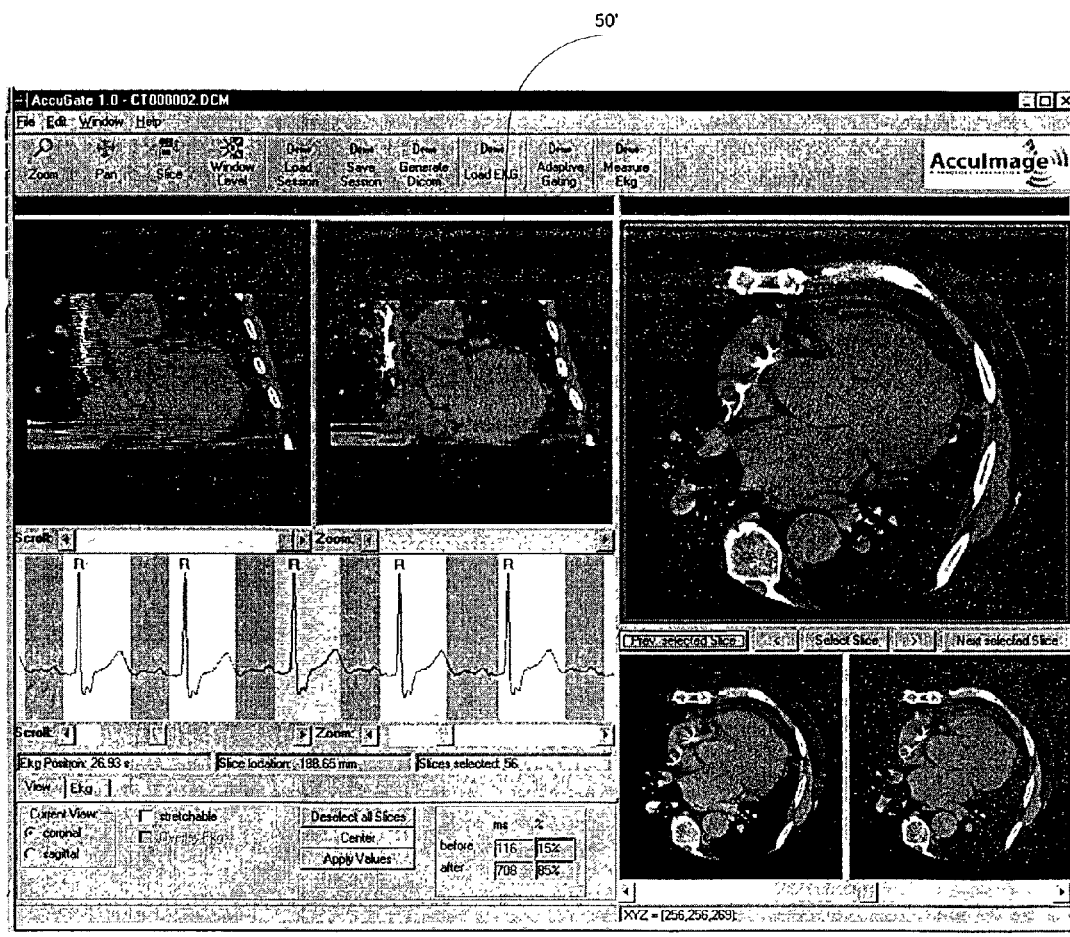
FIG. 5 illustrates a graphical user interface displaying slice images selected during a systole.

In exemplary embodiments, fourth screen section 52 can be toggled between an "ECG" screen 82 (FIGS. 2 and 3) and a "View" screen 84 (FIGS. 4 and 5). Once the View tab 83 is activated, a View screen 84 will be displayed. View screen 84 includes buttons 86, 88 that allow the user to change the view of the reconstruction image 50 between a coronal (or MPR3) and a sagittal (or MPR2) projection.

Fourth screen portion 52 can include an ECG tab 90 which when clicked or otherwise selected by the user will display ECG screen 82 so as to display information about the average length of the R-cycle for the patient for certain intervals of the ECG. In some embodiments, the ECG screen will have a graph which illustrates the duration of the patient's R-R cycle. Such a graph can graphically illustrate the duration of the R-R cycles, typically in milliseconds. Thus, if the R-R cycle is seen to be decreasing or increasing over time, the user can modify the method in which the slice images are selected.

For example, as shown in FIGS. 2 and 3, the graph 92 shows that the R-R cycle stays relatively constant through 30 measured R-R cycles. For such information datasets, selecting an absolute time before or after the R-wave will likely be sufficient to select the appropriate slice images for inclusion into the projection reconstruction. If, however, the patient had graph 94, which shows a change in the duration of R-R cycle over time (e.g., a slope in the graph), it would probably be beneficial to use a percentage of cardiac cycle as the selection criteria for the slices.

Once the user decides on a selection criteria, the user can activate View tab 83 to bring up View screen 84. View Screen will include fields that 96 allow the user to enter their desired selection criteria. View Screen 84 can also include an Apply Values button 98 that applies the slice selection criteria for the R-R cycles, a Deselect all Slices 100, Center the ECG image in the ECG field 102 and described more fully below.

If the Deselect All Slices button 100 is activated, the slices that were selected for inclusion in the reconstruction projection image will all be deselected and the user will be allowed to reselect the slice images for the reconstruction projection, using the slice selection criteria input into the specified field. Activation of the Center button 102 will center the ECG cardiac cycle within the ECG field for the image slice that is displayed in window 54.

Figure 6:
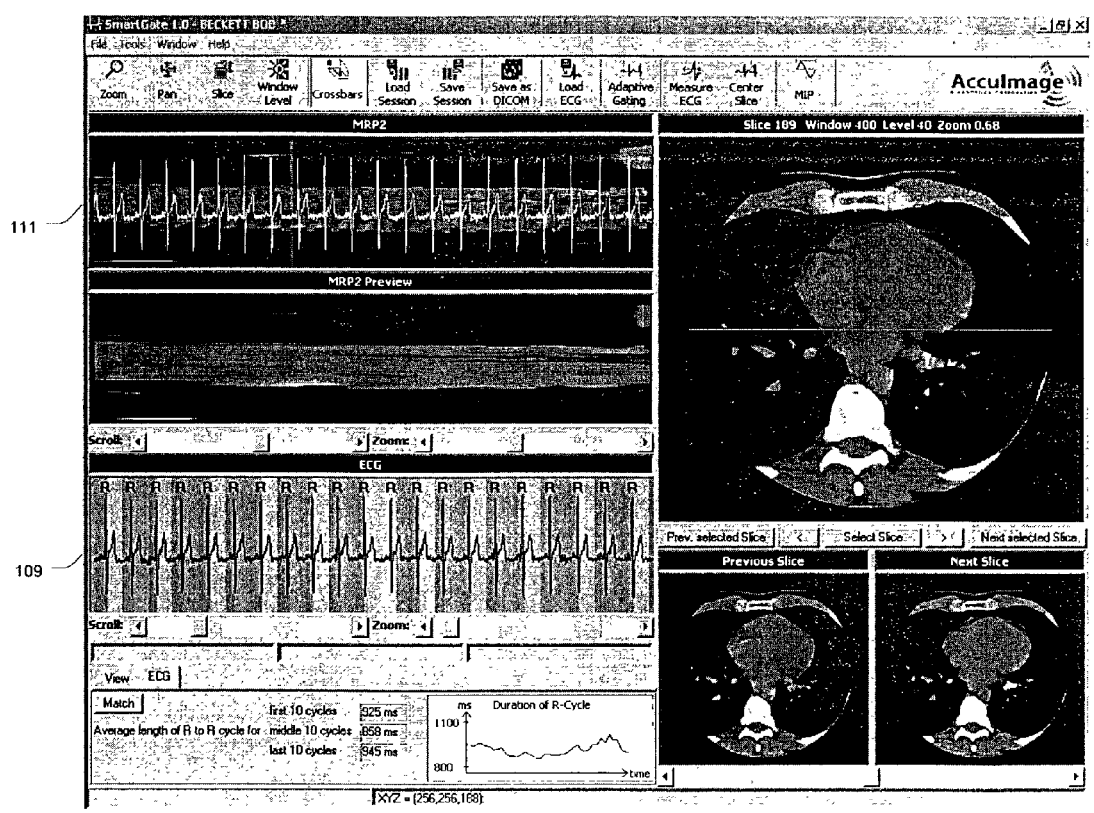
FIG. 6 is a graphical user interface displaying a stretched image and an overlaid ECG signal.

As illustrated in FIG. 6, in order to display a stretched image of the coronal and/or sagittal reconstruction projection, the user can activate a input box 105 in the fourth screen section. A stretched image allows examination as to whether a particular slice fits well with respect to its neighbors, or whether another slice may fit better.

Referring again to FIGS. 4 and 6, checking of the box will provide a stretched coronal or sagittal projection of the reconstruction of slices in third screen section 46. Checking of box 105 will make a "Display/Overlay ECG" box 107 active to allow the user to overlay an ECG signal over the stretched reconstruction projection. If desired, the user can overlay the ECG over the stretched image so as to allow the user to determine if a slice fits well with respect to its neighbors in a particular cycle, or whether another slice may fit better.

The stretched view is needed because the spatial resolution of the computer screen/eye combination is not sufficient to adequately view the image with the necessary detail. Zooming the image would require too large a space on the screen for the in-plane dimension, so that the image is zoomed only along the slice axis and thus appears stretched.

When displaying a stretched image with an overlaid ECG, fourth screen portion 52 can include a "Match" button 113. As shown in FIG. 6, the "Match" function will scale and zoom the stretched view of the ECG in window 109 to match the portion of the ECG displayed in window 111, the two ECGs being displayed synchronized. In addition, with the click of a button on the input device, the software of the present invention can also center the ECG and the stretched view on the current slice, in case it is scrolled out of the field of view.

If the user desires to replace a slice image from the stretched view, the user can scroll through the slices displayed in window 42 until the highlight marker 76 in the ECG field 70 is over the desired portion of the cardiac cycle within field 70. Thereafter, the user can activate the select slice button 64 to include the slice in the stretched view.

Referring again to FIG. 4, the user can choose to toggle between a coronal projection and a sagittal projection to alter the view of the projection image by activating the input field 86, 88. In other embodiments, it may be possible to activate both of fields 86, 88 so as to simultaneously display the coronal and sagittal projections.

The method of using the graphical user interfaces of the present invention will now be described. The software of the present invention can be a stand alone software package or it can be in the form of a plug-in into a software package, such as a calcium scoring package. First, the user can load an image scan, or a collection of slices acquired during imaging into the software. The image scan can be a saved image scan, or alternatively, the image scan can come directly from a CT scanner attached to the computer running the software of the present invention.

If available, ECG information that corresponds to the image dataset can also be downloaded into the software. If an ECG information is not available, the software can use the self gating methods described below, to gate the images. If an ECG is loaded into the software, the ECG will be displayed in ECG field 44 and a composite sagittal/coronal image of all of the slices of the image scan will be displayed in window 46. In some embodiments, a center slice of the image set and its two neighbors can be displayed in windows 54, 56, and 58. As can be seen in FIG. 2, the composite image with all of the slices will generally have a jagged outline due to the movement of the heart. To improve the selection of the slices included in the sagittal/coronal projection, the user can click on the ECG tab 90 to display the R-R cycle information.

After analyzing the R-R cycle information for any changes in the duration of the R-R cycle during the acquisition period, the user can choose from a plurality of selection criteria, typically either an absolute time period or percentage of cycle period. The user can select the View tab 83 and enter the selected criteria in the appropriate field 96. In some embodiments, if the user selects an absolute time selection criteria for a slice, the program will automatically calculate a corresponding percentage of cycle that corresponds to the absolute time entered by the user for that slice (Window 54). Similarly, if the user selects a percentage of cycle as the selection criteria, the software will automatically calculate and display a corresponding absolute time relative to the R-wave.

Once the user has entered the selection criteria, the user can activate the Apply Values button 98 to select the slices for inclusion into the projection image. As shown in FIG. 2, once the selection criteria value is applied, the user will be provided with a coronal/sagittal projection using only the selected slices in window 50 that is adjacent the coronal/sagittal projection using all of the selected slices. The ECG will also be highlighted 76, 78 to illustrate which slices are chosen and the position of the slices relative to the ECG.

FIG. 4 illustrates an coronal image 50 which was selected during the diastole. In contrast, FIG. 5 illustrates the coronal projection image 50' that was selected during systole. As can be seen in the images, the coronal projection image of the heart during systole is noticeably blurrier.

If the user desires to re-select the selection criteria, the user can again click on the View tab 83 and enter a new selection criteria (e.g., a new time or percentage value) until an acceptable coronal/sagittal projection image is generated. Advantageously, because the coronal/sagittal image is updated in real-time when the new slices are selected, the user can tell, in real-time, the effect of the choice of the images on the quality of the coronal/sagittal projection image.

Once the user has found an acceptable "global" selection criteria, the user can manually scroll through the slice images to select or deselect individual slice images of the image scan to improve the choice of the individual slice images. For example, as shown in FIG. 2, to scroll through the selected slices, the user can activate the Prev. Selected Slice button 66 and Next Selected Slice Button 68. Such buttons will display in window 54 the Selected slice and in windows 56, 58 the slices adjacent the selected slice. If the user wants to keep the slice displayed in window 54, the user can move to the next slice image by pressing either button 66 or 68. If however, the user wants to select another slice, the user can activate the Deselect button 65 and scroll through the adjacent slices by activating button 62, 63. Once the user finds a slice that is acceptable, the user can activate the Select button 64 (FIGS. 4 and 5). The user can repeat this process until all of the slices have been selected. Thereafter, the user can save the image scan (e.g., the selected slices, the sagittal/coronal projection, selection criteria, and the like), and the image of the heart with the selected slices can be calcium scored and/or 3-D rendered. The calcium scoring can be carried out by a separate software program, or it can be carried out by the same program that gated the image scan. Some exemplary computer systems for running the software of the present invention, calcium scoring methods, and software are more fully described in co-pending U.S. patent application Ser. No. 10/096,356, filed Mar. 11, 2002 and U.S. patent application Ser. No. 10/126,463, filed Apr. 18, 2002, entitled "Methods & Software for Improving Coronary Calcium Scoring Consistency," the complete disclosures of which are incorporated herein by reference.

In another aspect, the present invention provides methods and software for gating an image scan without the use of a gating signal. Because the gating signal (e.g., ECG signal) requires the purchase and use of additional expensive hardware and software packages, and requires added time for placing the electrodes on the patient and confirming the adequacy of the signal being obtained, it is often desirable to be able to perform an image scan without the use of a gating signal. Exemplary self-gating methods of the present invention use information derived from the image slices themselves to infer the heart motion without the use of an ECG signal.

In one self-gating method, the image slices are selected through detection of the size of the heart or pixel intensity in each of the slice images. In another self-gating method, image slices are chosen through deriving an average heart rate from the variability of the signal in the image data and selecting the images based on the calculated frequency information. In some configurations, a size of the heart is used in conjunction with the frequency measurement to generate the image of the heart.

During the quiescent time (e.g., diastole), the heart will be imaged in relatively motionless and fully expanded size. In contrast, when the heart is in systole, the heart will be contracted. By selecting the images in which the image of the heart volume is largest, the set of images will be selected when the heart is in diastole.

Figure 7:
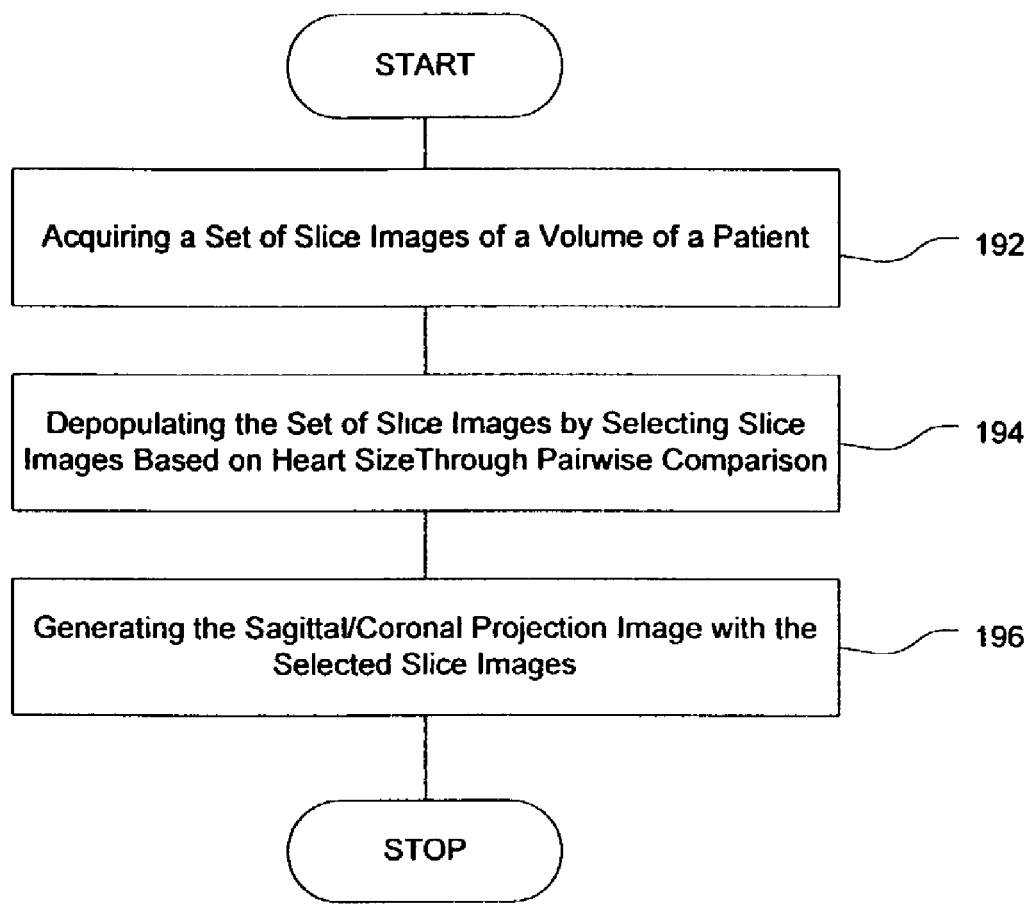
FIG. 7 schematically illustrates a simplified method of self gating a set of image slices.

In a first self-gating method illustrated schematically in FIG. 7, the software of the present invention selects slice images from the set of slices based on the size of the heart. The first step of the first method of self-gating the images is to acquire the set of overlapping images of the volume of the patient (Step 192). Selection of the images can be done successively by depopulating the slice set (based on the size of the heart in the image) until the necessary number of slice images are selected, enough to cover the heart without gaps, which depends on slice thickness and heart size. In one exemplary embodiment, depopulating the image scan can be carried out by pairwise comparison. (Step 194). Once the slice images are selected, the coronal/sagittal projection can be generated and the image of the heart can be calcium scored or 3-D rendered. (Step 196).

If in some of the methods of this invention there are gaps in the image data, before saving or calcium scoring the gated image, the user will be warned of the gaps and asked if the gaps should be filled. If the user chooses to fill the gap, the software can automatically fill the gap by selecting a slice image that is substantially in the middle of the gap.

By drawing on a sagittal or coronal view a region of interest (ROI) encompassing one side of the heart, one can determine the state of the heart muscle by noting the total signal along the line representing the slice, or noting how many pixels have the signal of muscle rather than the much lower signal of fat of the lung. When comparing a slice to its immediate neighbors, the slice with the most expansion will provide a line with a higher total signal, or with more pixels above a specified threshold, than a slice belonging to a point in time with less expansion. For pairwise comparison, each slice is compared to one neighbor, and the one with most expansion kept. This process can stop when a gap would be generated by further depopulation of the slices.

Figure 8:
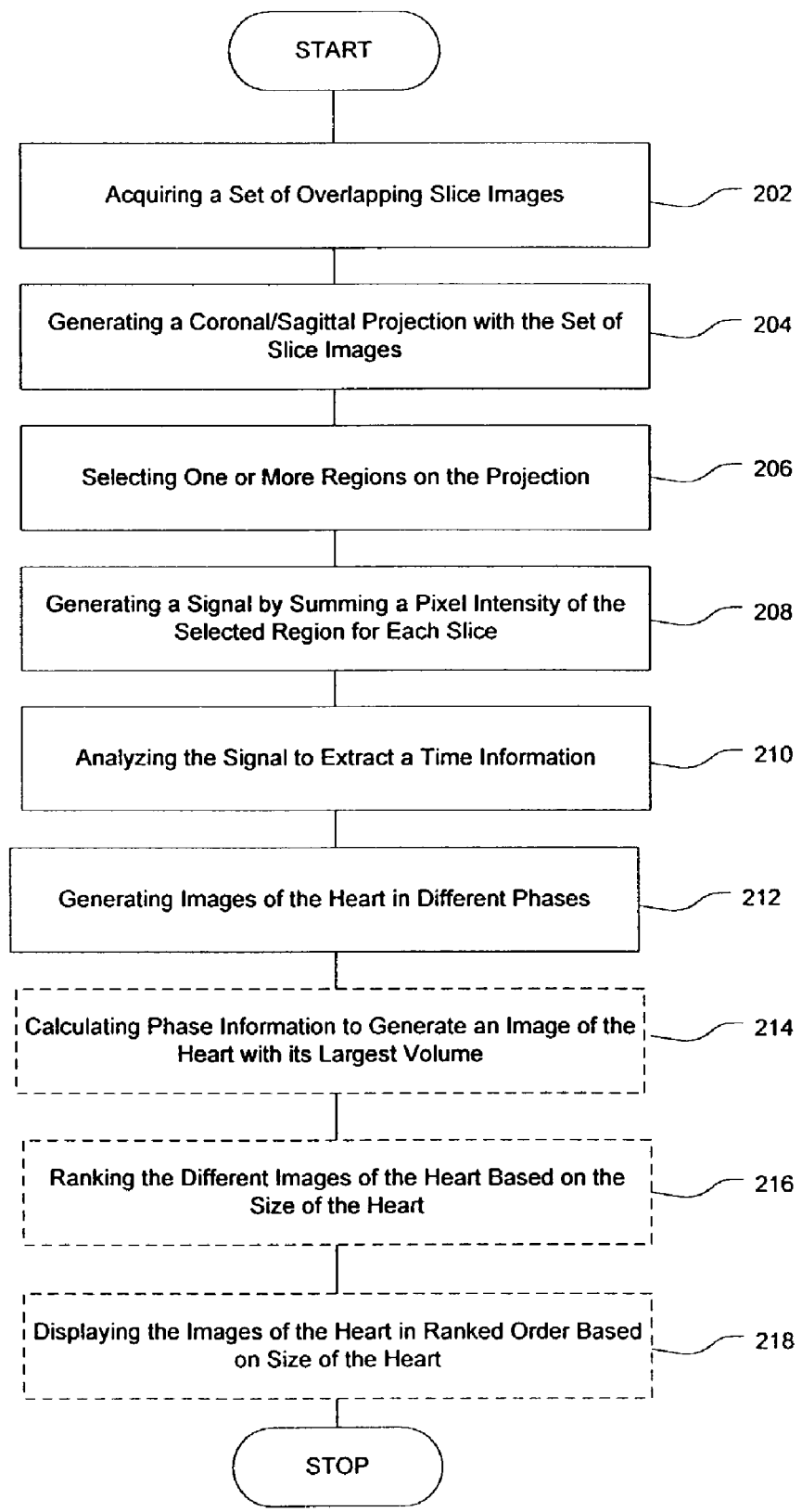
FIG. 8 schematically illustrates another simplified method of self gating as et of image slices with the optional steps in dotted lines.

FIG. 8 schematically illustrates another simplified method of self-gating in which the images are selected by finding the fundamental frequency of the heart from the images themselves. The exemplary method 200 comprise obtaining a set of overlapping slice images of a volume of the patient, typically of the patient's heart. (Step 202). As described above in relation to the retrospective gating, the set of images can be obtained with a CT scanner, or an equivalent imaging technology.

Figure 9A:
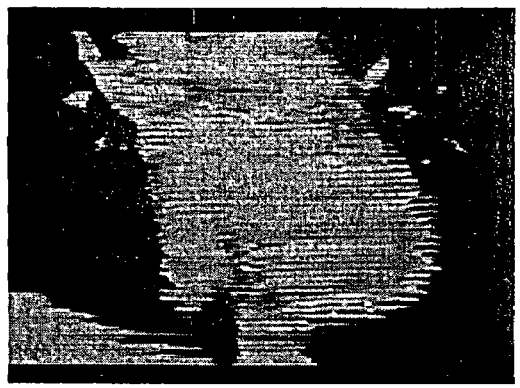
FIGS. 9A and 9B are coronal and sagittal projections of a patient's heart, respectively.
Figure 9B:
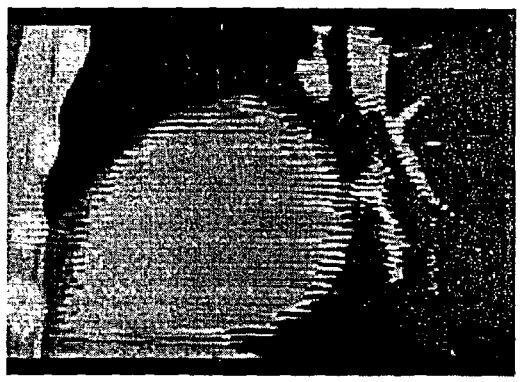

The set of images can be run through an algorithm to generate a coronal/sagittal projection of the volume of tissue of the patient. (Step 204). FIGS. 9A and 9B illustrate a coronal and sagittal projection of an image of a patient's heart. The images have jagged edges due to the motion of the heart.

Figure 10:
FIG. 10 illustrates a freehand editing of a region of interest.
Figure 11:
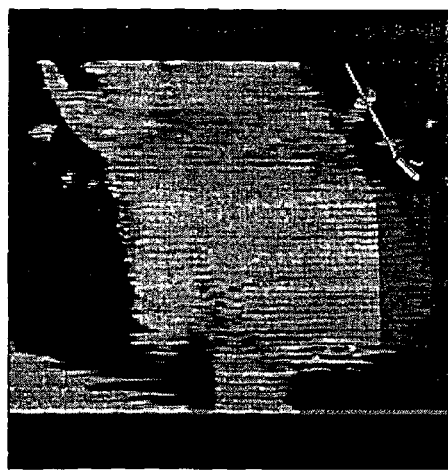
FIG. 11 illustrates a straight line editing of a region of interest.

The user can then highlight one or more region of the heart in the coronal/sagittal projection (Step 206). Generally, the user can select some region around the jagged outline of the heart. More distinctive outlines around the heart will give better results. In exemplary embodiments, the regions of the heart can be marked with a freehand region (FIG. 10), a straight line region (FIG. 11). Due to the scanner rotation time, the outline of the heart is generally only selected on one side of the heart-outline. It should be appreciated however, that other conventional marking methodologies can be used to mark a region of the image, including the use of automated boundary-finding algorithms.

A pixel intensity signal of the images can be generated by summing the pixel intensities (HU) within the selected region for each slice in a direction that is perpendicular to the slice direction. (Step 208). The result of the summation is a signal graph, as illustrated in FIG. 12. The signal graph will produce a plurality of maximas and minimas, wherein each of the maximas generally corresponds to a maximum inflation of the heart. The position along the horizontal axis corresponds to the slice number. The intensity is 0 for slices not included in the selection. The intensities can be corresponded to the slices, each of which is acquired at a certain point in time, usually every 100 ms. It should be appreciated however, that the point in time in which the image acquisition is performed will vary depending on the patient's heart rate or other factors, and such parameters can be set accordingly.

The signal can be analyzed to extract the time information from the images. (Step 210). Extracting the time information from the signal can be carried out through an analysis of the frequency spectrum and/or through analysis of local intensities of the signal.

In one exemplary method of extracting the time information, a Fourier transformation is applied to analyze the frequency components of the signal. In the Fourier transformation, the amplitude profile is viewed as a function of frequency. Each function can be represented through its Fourier components—by combining a number of sine and cosine functions of different frequencies. The signal intensity profile of the slices will provide a repetitive maxima and minima. The sinusoid (e.g. sine or cosine function) of the same frequency as the repetitive pattern will have a large contribution. The goal is to find this principal component, the sinusoid of the corresponding frequency.

The result of the Fourier analysis will be a series of complex numbers. Each number corresponds to a sinusoid of a certain frequency. The formula is:

$$F(k) = \frac{1}{M}\sum_{m=0}^{M-1} f(m)e^{\frac{-2\pi imk}{M}}$$

where m is the slice number, M is the total number of slices and k is the coordinate in frequency space (or k-space) and k/M is the frequency which corresponds to value F(k), From the Fourier analysis, information about the magnitude and phase of the sinusoid can be obtained. The magnitude indicates the strength of any one frequency component, including the principal component. For each component there is corresponding phase information which contains information about where that component begins. While the phase can theoretically be obtained from this phase information, in practice, the phase is changing very fast as a function of frequency, and the measurement is not reliable.

To find the frequency which is the most dominant portion of the function, only the information about the "energy" for each frequency component is necessary. The energy of the sinusoid can be read from the power spectrum, in which power is defined by:

$$Power(k) = Re(F(k))^2 + Im(F(k))^2$$

where Re is the real part of the complex number F(k) and Im is the imaginary part of the complex number F(k). The result will be a sequence which contains only real values. One example of a power spectrum is illustrated in FIG. 14.

After the power spectrum is computed, the Fourier series can be smoothed with a Gaussian filter to reduce spurious peaks. Because the task of finding the heart beat is circumscribed by physiologic restrictions, the present invention can restrict the search for the maximum frequency to a range of approximately ½₀₀₀ ms and ⅕₀₀ ms, which corresponds to an interval of 500 ms to 2 seconds between two heart beats.

Thereafter, the absolute maximum value in the power series and frequency can be determined. Additionally, the lower and higher frequencies next to the maximum frequency where the value is half of the maximum value can be measured (noted as the half-height interval in FIG. 14). If the maximum frequency and the half-height interval are found, the frequency which is directly in the middle of the interval defined by the half-heights is used as the "maximum." If, however, the half-height interval can not be determined, the absolute maximum can be used as the "maximum." From the maximum frequency, the fundamental frequency (e.g., the heart beat) of the heart can be determined.

From the Fourier transformation, the software can determine the fundamental frequency of the heart and generate images of the heart in different phases of the heart cycle. As will be described below, the user can display a plurality of projection images of the heart, in which each of the images corresponds to a different phase of the heart cycle.

Because it is difficult to extract the phase information present in the Fourier spectrum, the Fourier transformation does not inform the user as to which slices represent the diastolic phase, systolic phase, and the like. Moreover, such a transformation does not account for irregular heartbeats or a changing of the heartbeat over the image acquisition period. In order to determine which slices correspond to the diastole, the software of the present invention can analyze the slice images to find the biggest heart volume image (e.g., the diastole) in which the heart motion is the least.

To determine the phase of each of the slices, (e.g., to determine which slices correspond to diastole), a local intensity signal of the slice images can be run through a derivative filter to produce a graph such as FIG. 13. Generally, this method can be used in conjunction with the results from Fourier analysis, as described above, to find the size of the heart in each of the slice images. With the frequency derived from Fourier analysis and phase from the local maxima, slice selection can be extended beyond the ROI of Step 206. It should be appreciated however, that it may be possible to use the local intensity profile as an independent algorithm. In such embodiments, the user would need to cover all slices with the selected region of Step 206.

In such an analysis, as illustrated in FIG. 13 each local peak 220 in the intensity signal corresponds to the maximum inflation of the heart. The peaks can be located through a differential analysis with the differential filter in which each peak (i.e., local maximum) has a first derivative of zero and a second derivative that produces a zero crossing response.

From the filtered data, the zero-crossings can be located. A crossing from a negative number to a positive and back to a negative corresponds to a maximum. Crossing from a positive to a negative and back to a positive corresponds to a minimum. It should be appreciated however, that the signs of the zero-crossings are dependent on the sign of the second derivative filter, which as described above was fixed to be negative-positive-negative. From the zero crossing intervals, the location of the maximum intensity values are found and the slices in which the heart is in diastole are chosen.

Post-processing of the maxima found above can proceed in several passes over the slice selection. As an initial step, the distance between two adjacent selected slices will be checked to determine if the slices are too close together. In one configuration, the slices will be deemed to be too close if they are within one third of the heart-rate frequency found by the Fourier transformation, this being a reasonable limit for how much the heart rate may change during the study. It should be appreciated however, that in other configurations, a smaller or larger frequency distance can be used. If the slices are deemed to be too close, the slice that has the lower intensity value will be removed from the image set of selected slices.

Next, for each selected slice, the algorithm can resample the images to verify that at least two of the slices' four neighbors are within 30% of the heart rate measured by the Fourier analysis so as to avoid irregular spacing. If the slice is outside of the 30% range, the slice will be deleted from the set of selected slices. It should be appreciated however, that it may be possible to use a criteria different criteria (i.e., smaller or larger than 30% of the heart rate), if desired.

Thereafter, the algorithm can resample the images to check the spacing between the remaining slices to see if there are any gaps that are bigger than the slice thickness (which is combination of the thickness of the slice for a stationary scan and the broadening introduced by the travel of the patient bed during the helical scan). If there is such a gap, the gap can be filled in with a slice of maximum intensity in FIG. 13 in the location of the gap. It should be noted, that it is preferable to have the slices be spaced so as not to leave gaps not covered by the slice thickness, as noted above. If there are any slices between two slices that are within the heart rate found by the Fourier analysis, the slices are deleted from the set of selected slices.

Generally, the derivative filter algorithm will only cover the selected region of the scan that was marked by the user. Thus, if the user did not select the entire image additional slices need to be selected. If slices need to be added, a pseudo-selection of slices can be generated on each end of the selection region. The generated slices will be spaced by the frequency found by the Fourier analysis. A cross-correlation at various offsets can be performed to obtain the best estimate of the phase for extension of the frequency information. The offset that returns the biggest correlation value is used to extend the dataset to complete the image. The same cross-correlation algorithm can be applied to the pseudo selection slices, as described above.

The computed heart rate can then be used to generate multiple slice subsets from the original set of slice images, in which each of the slice subsets correspond to a different phase of the heart cycle. (Step 212). The present invention can use software to efficiently select as many sets as there are redundancy, and present them to the user for selection. Multiple selections can be generated from the frequency but at different phases of the cardiac cycle to give the user the choice to select one. There are (1/frequency*1/time between slices) different offsets from the first slice in the original image set. The software program selects the $i^{th}$ slice as offset+i*(1/frequency*1/time between slices) so as to result in 1/frequency*1/time between slices subsets of the original scan. The user can choose the desired set from these.

Having the fundamental heart rate, however, is not sufficient for the best selection of slices since the fundamental heart rate does not explicitly define which slices correspond to the diastolic phase. Thus, to select the images that were obtained during diastole, the heart frequency information can be used along with the information obtained with the derivative filters to obtain time and phase information to generate an image in which the heart is at its largest volume (e.g., diastole). (Step 214).

Additionally or alternatively, the plurality of images of the heart can be ranked by applying a quality measure so as to rank the images based on heart size. (Step 216). One quality measure algorithm comprises summing all of the pixel intensity values over a certain threshold value. The intensity value is normalized by the total number of pixels in the image to provide the average intensity value of the image. Thereafter, each of the average intensity values of each of the images are compared to rank the images relative to each other.

Another quality measure algorithm counts the number of pixels above a threshold value. The number of pixels above the threshold is normalized by the number of pixels in the image to provide a fraction. The fraction can identify the percentage of the image that the heart occupies in the image. Generally, the higher the fraction, the better the selection. Thereafter, the fractions of each of the generated images are compared and ranked relative to each other. It should be appreciated however, that other quality measure algorithms can be used to rank the images of the heart.

Thereafter, the images of the heart can be displayed on a computer output display in order of rank so as to allow the user to select the phase most appropriate for the scoring of each vessel within the heart. (Step 218). Alternatively, it may be possible for the software to automatically display only the image with the highest rank.

In some methods, the software of the present invention can be used to auto correlate between image pairs and computes the quality of the correlation. Times of slow motion produce better correlations than when the motion is rapid. A repetitive pattern can be established from which the quiescent times are selected to create the gated image set. Advantageously, the same graphical user interface of FIG. 2 can be used to gate the image scan.

FIG. 15 illustrates a graphical user interface that can be used to self-gate the set of image slices without the use of an ECG signal. As shown in FIG. 15, menu toolbar 53 can include additional buttons "Edit," "Clear Selection," and "Self Gate" that allows the user to self gate the image scan. The software allows the user to delineate the regions of the heart where the heart motion can be visually observed.

With the "Edit" button 110, the user can enter an editing/drawing mode in which the user can draw a boundary around a region of the image of the heart and mark it. The region can be selected by at least two different manners. A first manner is through a straight line selection, in which the user selects a first end point of a straight line and a second end point of the line to define the region.

In selecting the region, the region must have a minimum length across the slice direction and a maximum length within the direction of one slice. If the selected region is too small to obtain enough information for analysis (e.g., less than about three seconds) or too wide so that the signal is lost because of scanner rotation (e.g., more than approximately half of the image width), the software of the present invention can provide the user with an error message to prompt the user to select a different region and to prevent the computation of a heart-rate from unsuitable data.

In exemplary embodiments, a left click of the mouse defines the first endpoint, and a right click of the mouse defines the second point. The line drawn by the user will be used to define a diagonal of a rectangular region. In a second manner, the user can use a freehand selection, which allows the user to select a region of arbitrary shape. In one embodiment, the user can depress a "Control" key on a keyboard of a computer system and move the mouse to draw the region of interest into the arbitrary shape. Releasing the control key closes the region. It should be appreciated however, that the above methods of drawing the region are merely examples, and other conventional methods of drawing/selecting the region can be used.

The region can be a portion of of the border of the patient's heart. Advantageously, drawing the region around multiple portions of the border of the heart allows the user to see and track differentially the motion of the heart through the different portions of the heart cycle. Thus, the user can view the different chambers of the heart as it moves through the R-R cycle.

The "Clear Selection" button 112 can delete a region that was previously marked by the user. The "Self Gate" button 114 starts the self gating procedure that is described herein.

Referring again to FIGS. 10–12, to self gate an image scan, the user marks selected section(s) in the sagittal view or the coronal view on one side of the heart where the motion can be seen. Motion of the heart will be shown by the jagged edge of the heart in the sagittal image and coronal image. Straight line boundaries 118 (FIG. 11) or freehand boundaries 120 (FIG. 10) can be drawn on one or more portions of an edge of the heart. If desired, the user can select multiple regions.

Figure 16:
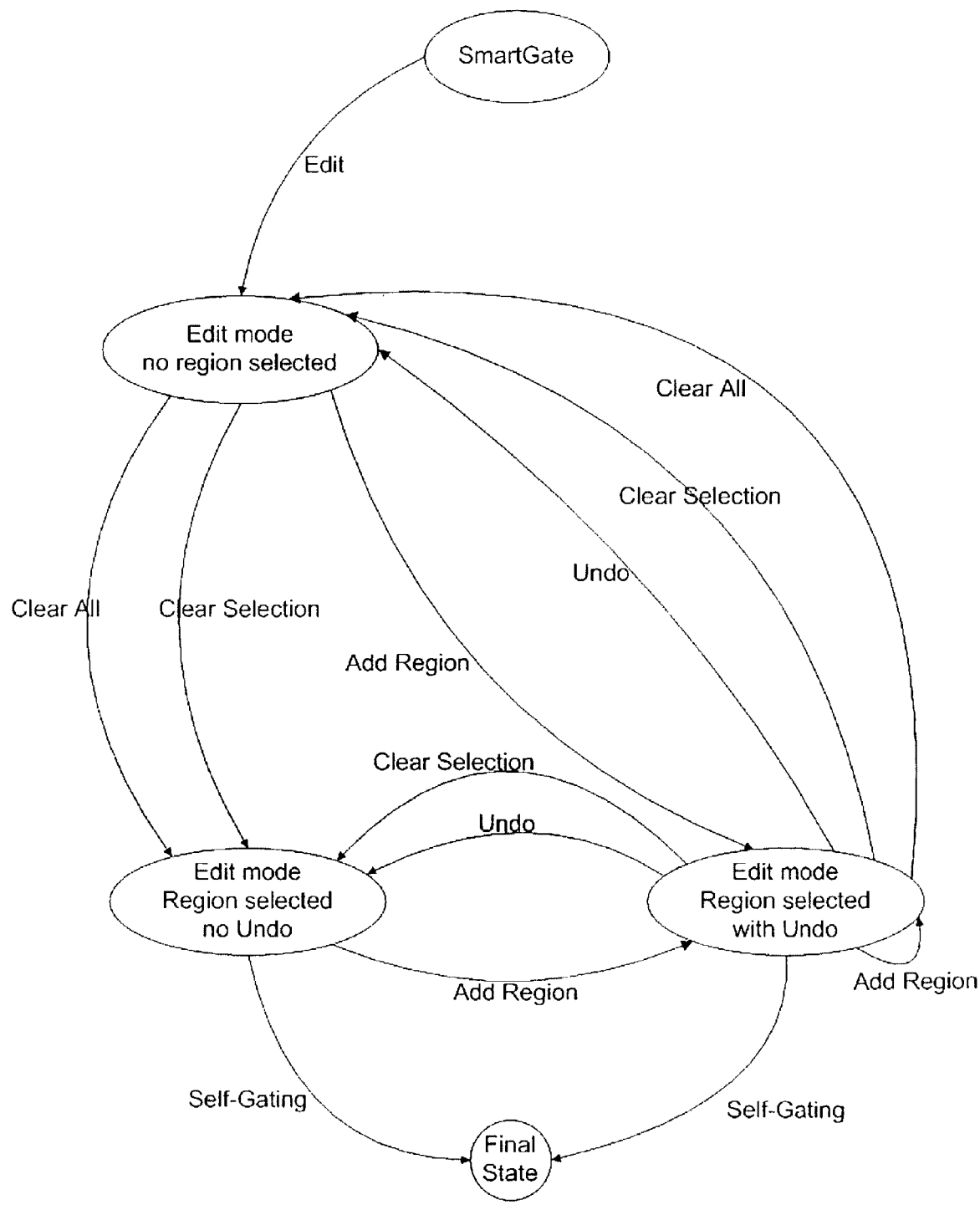
FIG. 16 is an exemplary data flow diagram of self gating.

Once the regions have been selected, the user can click on the Self Gate button 114. The self gate software can them compute the average frequency of the heart beat using the information of the selected region and generate a number of selection. FIG. 16 schematically illustrates an exemplary data flow of the present invention.

Figure 17:
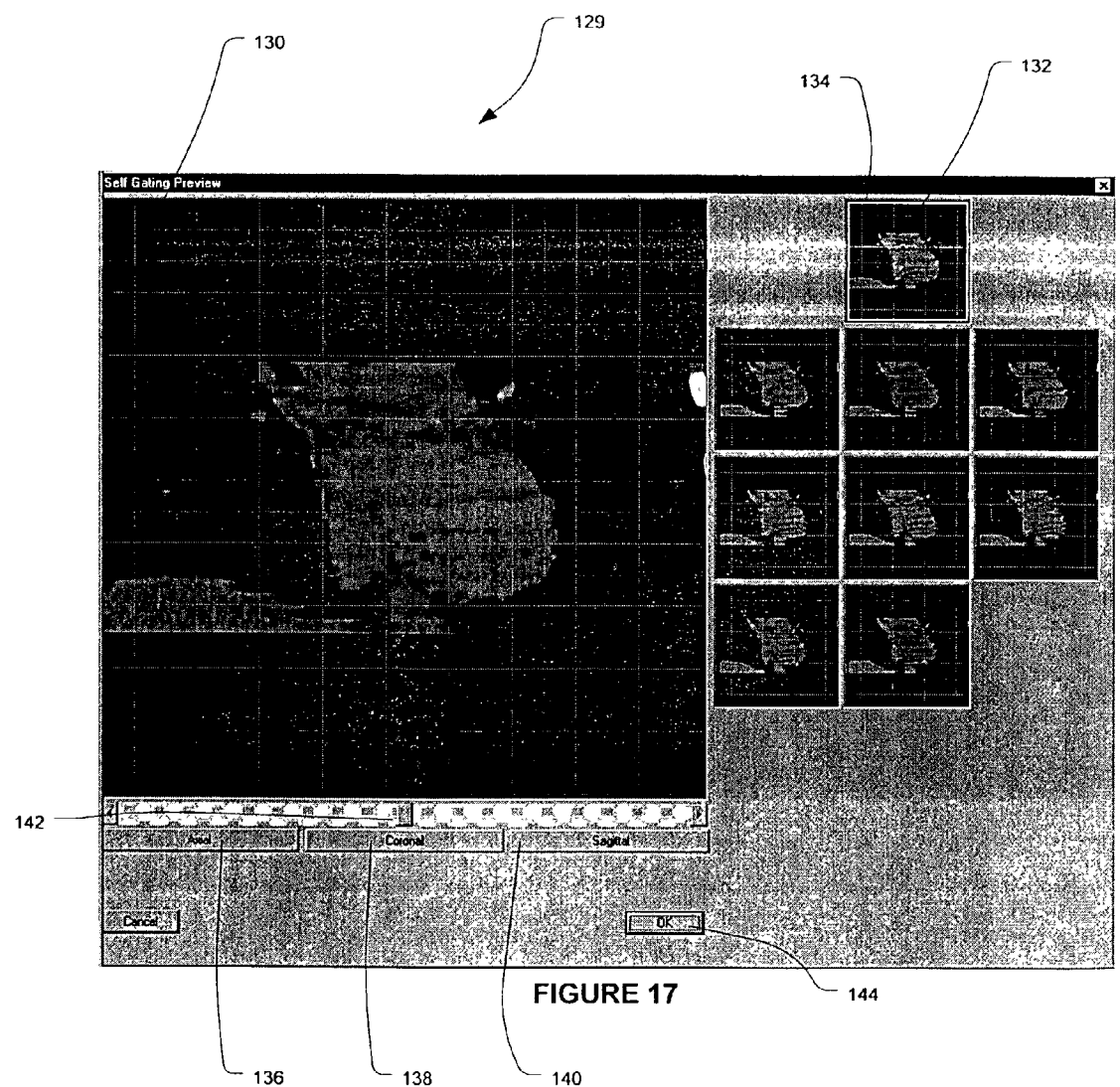
FIG. 17 is a graphical user interface of a self gating preview.

FIG. 17 shows one preview screen graphical interface for displaying the multiple selections. One selection represents the biggest heart volume based on the frequency information of the selected region and the intensity values in the marked regions. The other selections are based only on the frequency information. Each selection corresponds to a different phase of the measured heart frequency.

As shown in FIG. 17, the preview screen 129 includes a main preview window 130 having the current selection. The default selection is derived from the selection that includes the intensity and frequency information. A smaller image 132 of the current selection can also be displayed alongside the right portion of the graphical user interface in one of the small preview windows and can be framed by colored frame 134. Clicking or otherwise selecting on another image alongside the small preview windows (e.g., the right portion of the graphical user interface) will display the selected image on the main preview window. The topmost image 132 shows the selection inferred by intensity and frequency information derived from the image scan. The remaining images show selections that use only the computed heart frequency at different offsets (e.g., different phases of the heart's motion). As seen in FIG. 17, many of the images at the different phase of the heart has noticeable blurring due to the motion of the heart. Nonetheless, providing a plurality of images of the heart in different phases allows the user to visually determine which heart image is best.

The user can select different projection of the current preview by activating the Axial button 136, Coronal button 138, or Sagittal button 140. The slider 142 can be activated by the user to scroll through the slice projections, if desired. When the user finds a projection image that is acceptable, the user can click on the OK button 144, which will apply the current selection and return to the main screen of the graphical user interface (FIG. 2).

As described above, once the selected image set is deemed acceptable, the image set can be calcium scored and saved. Before saving the slices as a new DICOM series, the selection of images can be checked for gaps. If there are gaps, the number of gaps can be reported to the user with their size range. The user can then select to ignore the gaps or can elect to fill in the gaps that are bigger than a specified threshold, which the user can specify.

One method of filling in the gaps is with a slice closest to the middle point between the selected slices. Of course, these gaps may also be filled through low order interpolation algorithms such as nearest neighbor, and in increasing order, linear, cubic and so on, or Fourier interpolation.

In another aspect, the present invention provides improved methods and software for calcium scoring the images. Retrospective gating often causes mismatches between the scanner rotation and the heart rate. Consequently, the selected images may not always be equally spaced such that there are gaps between the images. Most calcium scoring algorithms, however, are based on algorithms that require a fixed spacing between the slice images.

Unfortunately, conventional linear or other low order interpolation schemes that can be used to generate equally spaced slice images from the selected merely blur the images, which degrades the calcium scoring of the images. The present invention provides a Fourier Interpolation that can rescale the dimensions of the image slices that does not introduce blurring or degrade the resolution. A more complete description of Fourier Interpolation can be found in U.S. Pat. Nos. 4,908,573 and 5,036,281 and in Kramer D. M., Li A, Simovsky I, Hawryszko C, Hale J and Kaufman L., "Applications of Voxel Shifting in Magnetic Resonance Imaging," Invest Radiol 25:1305, 1990, the complete disclosures of which are incorporated herein by reference.

While all the above is a complete description of the preferred embodiments of the inventions, various alternatives, modifications, and equivalents may be used. Although the foregoing invention has been described in detail for purposes of clarity of understanding, it will be obvious that certain modifications may be practiced within the scope of the appended claims.

What is claimed is:

1. A method of selecting slices from an image scan, the method comprising:
   acquiring a plurality of overlapping slice images of a patient with a CT scanner;
   acquiring an ECG signal of the patient during the acquiring of plurality of overlapping slice images;
   choosing a first set of slice images from the plurality of overlapping slice images based on a timing of the slice image relative to the EGG signal;
   applying a maximum intensity projection algorithm to each slice image of the first set of slices and slices immediately adjacent the slice images in the first set to generate a maximum intensity projection slice image that contains, on a pixel by pixel basis, information from a pixel with the highest intensity in the three slice images; and
   generating a second set of slice images from the maximum intensity projection slices.

2. The method of claim 1 comprising generating a coronal or sagittal reconstruction with the second set of slice images.

3. The method of claim 1 wherein the EGG signal comprises a plurality of cardiac cycles, wherein each of the cardiac cycles includes an R-wave,
   wherein choosing comprises selecting slices that are at an absolute time period before or after the R-wave.

4. The method of claim 1, wherein the EGG signal comprises a plurality of cardiac cycles, wherein each of the cardiac cycles includes an R-wave,
   wherein choosing comprises selecting slices that are a percentage of the cardiac cycle before or after the R-wave.

5. The method of claim 1 comprising calcium scaring the second set of slices.

6. The method of claim 1 comprising 3-D rendering the second set of slices.

* * * * *